United States Patent [19]

Benyaev et al.

[11] 4,302,543

[45] Nov. 24, 1981

[54] PROCESS AND APPARATUS FOR PRODUCING STARCH-CONTAINING FEEDSTOCK HYDROLYSATES FOR ALCOHOLIC FERMENTATION

[76] Inventors: Negmat E. Benyaev, ulitsa I Parkovaya, 43, Moskovskaya oblast, Mytischi; Razmik A. Boskanian, ulitsa Butlerova, 18, kv. 36, Moscow; Viktor I. Yarovenko, ulitsa Panfilova, 18a, kv, 16, Moscow; Jury N. Durbrov, ulitsa M. Dzhalilya, 34, korpus 2, kv. 278, Moscow; Boris A. Ustinnikov, 6 Parkovaya ulitsa, 13, kv. 92, Moscow; Ljudmila V. Babichenko, Teply Stan, 18, kv. 36, Moscow; Mikhail D. Vakulenko, ulitsa Jun. Lenintsev, 79, korpus 3, kv. 265, Moscow; Nikolai A. Kramarsky, ulitsa Khalturinskaya, 11, kv. 43, Moscow; Vitaly F. Shamrin, ulitsa Tambovskaya, 207, kv. 11; Sergei I. Karaichev, ulitsa Tambovskaya, 207, kv. 9, both of Michurinsk Tambovskoi oblasti; Boris V. Efremov, Sudostroitelnaya, 7, korpus 2, kv. 170, Moscow; Tatyana N. Lantsetova, ulitsa Bobruiskaya, 12, kv. 74, Moscow, all of U.S.S.R.

[21] Appl. No.: 125,767

[22] Filed: Feb. 27, 1980

[51] Int. Cl.$^3$ ................................................ C12P 7/06
[52] U.S. Cl. .................................... 435/161; 435/93; 435/99; 435/316
[58] Field of Search ........................... 435/93, 99, 161

[56] References Cited

U.S. PATENT DOCUMENTS 4,062,728  12/1977  Blanchard ............................ 435/99

FOREIGN PATENT DOCUMENTS 1540552  2/1979  United Kingdom .

*Primary Examiner*—Lionel M. Shapiro
*Attorney, Agent, or Firm*—Steinberg & Raskin

[57] ABSTRACT

A process for producing hydrolyzates of a starch-containing feedstock for an alcoholic fermentation which comprises extrusion of a preliminary disintegrated feedstock at a temperature of 150°–300° C. under a pressure of $2.10^5$–$2.10^8$ Pa, followed by fermentative hydrolysis of the extrudate. The extrudate is mixed with an aqueous enzymatic solution and hydrolyzed for 30–60 minutes by creating direction vortical streams by means of a source thereof at a rotation speed of 1,000–6,000 r.p.m. with simultaneous change of their direction.

An apparatus for the process according to this invention comprises, mounted downstream; a receiving bin, a lifting mechanism, balance, feeder, separator for separation of foreign matter, disintegrator, extruder and means for fermentative hydrolysis. This means is in the form of a cylindrical vessel with a cover. Inside the vessel there is a source of opposite-direction vortical streams comprising at least two horizontally mounted perforated discs, one being ridigly secured to the inner surface of the vessel, the other mounted under the first one and rigidly fixed on a rotating shaft mounted along the vessel axis; and at least six ribs with three of them being ridigly fixed on the inner surface of the vessel parallel to its axis, the three others being radially mounted on the cover.

The present invention makes is possible to increase the amount of soluble sugars in the starch-containing feedstock hydrolysates and the yield of food-grade ethanol by at least 2%.

1 Claim, 2 Drawing Figures

PROCESS AND APPARATUS FOR PRODUCING STARCH-CONTAINING FEEDSTOCK HYDROLYSATES FOR ALCOHOLIC FERMENTATION

FIELD OF THE INVENTION

The present invention relates to the food industry, more particularly to the alcohol-production industry, and more specifically, to a process and apparatus for producing hydrolysates of starch-containing raw material for alocholic fermentation.

The present invention is useful in the production of alcohol and starch-syrup, as well as in the brewery and confectionery industries.

BACKGROUND OF THE INVENTION

Known in the art is a multi-stage process for producing hydrolyzates of a starch-containing feedstock (cf. U.S. Pat. No. 4,062,728; Cl. 195-31, 1977).

The process comprises disintegration of the starch-containing feedstock, liquefaction of starch in the presence of α-amylase at a temperature of from 100° to 110° C. for 3 minutes and then also for 3 minutes at a temperature of 140° C. under a pressure sufficient to provide for the liquid state of the starch-containing feedstock. The resulting liquefied suspension of starch is subjected to instant evaporation in the atmosphere thus reducing the pressure to atmospheric and causing cooling of the suspension.

Thereafter the suspension is subjected to repeated liquefaction under atmospheric pressure at a temperature of from 90° to 100° C. in the presence of an additional amount of α-amylase.

Also known in the art is a process for producing hydrolysates of a starch-containing feedstock for a wort (cf. Japanese Patent Application No. 1,540,552 published Feb. 14, 1979).

According to this process, barley is gelatinized and, when required, liquefied by the fermentative method by heating under pressure, for example in water or in an extruder, whereafter the gelatinized product is subjected to fermentative hydrolysis in the presence of α-amylase at a temperature within the range of from 50° to 60° C.

The gelatinization process does not ensure a 100% conversion of starch from the feedstock to the soluble state.

Also known is a process for producing hydrolysates of a starch-containing raw material for alcoholic fermentation and an apparatus therefor (cf. D. N. Klimovsky, V. A. Smirnov, V. N. Stabnickov "Alcohol Technology", Moscow, 1967).

In this process the purified and weighed starch-containing feedstock, e.g. grain, is transported, by means of a conveyor, to disintegration, whereupon it is milled to a 100% passage thereof through a sieve with a cell of 1 $mm^2$. The disintegrated grain is fed to a mixer, into which water is also supplied to form a kneading mass. Then the grain kneading mass is fed to the heat-treatment - cooking of the feedstock. The cooking is effected in three series-connected apparatus: pre-cooker, cooking column and after-cooker.

The pre-cooker comprises a horizontal cylindrical vessel provided with a stirrer. A steam inlet pipe is mounted in its lower section. The grain kneading mass is hetaed here to a temperature of 80°-85° C. and kept for 4-5 minutes.

From the pre-cooker the kneaded grain mass is fed to a cooking column, wherein it is heated to a temperature of from 120° to 150° C. by steam admitted under a pressure of from 3 to 4 atm.

From the cooking column the mass overflows into an after-cooker, wherein it is additionally cooked at a temperature of from 140° to 150° C. without the supply of live steam.

The duration of residence of the mass in the cooking column is 25 to 30 minutes, in the after-cooker 25–30 minutes so that the total residence time is 50–60 minutes.

After the heat-treatment the feedstock is cooled to a temperature of 58°-60° C. and delivered into an apparatus for the fermentative hydrolysis, into which an aqueous enzyme solution is added in a ratio of 1:3-4.

The hydrolysis is conducted for 50–60 minutes under stirring, effected for example by an impeller. In this case an intensive stirring of the solution is not ensured, dead zones are formed in the apparatus, thus causing a non-uniform distribution of the solution in the apparatus.

During the heat-treatment of the starch-containing feedstock there are formed non-condensed gases and volatile organic substances which cause corrosion of the apparatus and, as a result, impair the quality of the produced food-grade ethanol. The high temperature employed in the heat-treatment of the starch-containing feedstock contributes to an increased rate of corrosion of the process equipment.

The heat-treatment of the feedstock at a temperature corresponding to the used pressure of saturated steam is associated with increased losses of the starch contained in the feedstock due to acceleration of the sugar-amine reaction. An excessive amount of the extra-steam is formed which is difficult to utilize. Furthermore, the output of the alcohol from a unit weight of the feedstock is reduced, while the rate of power consumption for the heat-treatment of the feedstock is increased.

These disadvantages result in a reduced service life of the equipment for the heat-treatment of the starch-containing feedstock and, in certain cases, even in a breakdown.

Further disadvantages are such as a long duration of the process of cooking of the feedstock under a high pressure (up to 60 minutes) necessitating a large volume of the process equipment and a large floor area occupied thereby.

SUMMARY OF THE INVENTION

It is an object of the present invention to accelerate the process and increase the amount of soluble sugars in hydrolysates starch-containing feedstock.

It is another object of the present invention to intensify the process of fermentative hydrolysis and increase the yield of alcohol.

It is still another object of the present invention to improve conditions of the apparatus operation and reduce its size.

These and other objects of the present invention are accomplished by the process for producing hydrolysates of starch-containing feedstock for an alcoholic fermentation by way of disintegration of the starting starch-containing feedstock, heat-treatment of the disintegrated feedstock, followed by mixing of the heat-treated feedstock with an aqueous enzymatic solution in a ratio of 1:3-4 for carrying out a fermentative hydrolysis. In accordance with the present invention the disintegration of the starting feedstock is effected to a particle size of 1–3 mm, and the heat-treatment is effected by extrusion of the disintegrated feedstock at a temperature within the range of from 150° to 300° C. under a pressure of from $2.10^5$ to $2.10^8$ Pa, the fermentative hydrolysis being conducted for 3 to 60 minutes by creating opposite-direction vortical streams of the resulting mixture by means of a source of opposite-direction vortical streams forming said streams at a rotation speed of from 1,000 to 6,000 r.p.m. simultaneously with change of their direction.

The disintegration of the starting feedstock to a particle size of from 1 to 3 mm makes it possible to lower power consumption for the process of the feedstock disintegration.

The use of extrusion totally replaces process of the feedstock heat-treatment in an aqueous medium at elevated temperatures and pressures utilized in cooking apparatus. Carrying out the fermentative hydrolysis under these conditions makes it possible to intensity the process of dissolution of the extrudate.

The process according to the present invention is effected in an apparatus comprising the following assemblies and means positioned downstream: a receiving bin, lifting mechanism, balance, feeder, separator for separation of foreign matter, disintegrator, a heat-treatment means and a means for fermentative hydrolysis. According to the present invention, in this apparatus the means for heat-treatment is in the form of an extruder and the means for the fermentative hydrolysis is in the form of a cylindrical vessel with a cover having located therein a source of opposite direction vortical streams comprising at least two horizontally mounted perforated discs, one of which is rigidly secured to the inner surface of the cylindrical vessel and the other of which is mounted under the first disc in close vicinity thereto and rigidly fixed on a shaft rotatably mounted along the axis of the cylindrical vessel, and at least six ribs three of which are rigidly fixed on the inner surface of the cylindrical vessel parallel to its axis and the other three on the cover and positioned radially.

The use of this apparatus makes it possible to avoid use of cooking apparatus, considerably reduces production floor area and provides a greater safety of operation.

BRIEF DESCRIPTION OF THE DRAWINGS

Other objects and advantages of the present invention will become more fully apparent from the following detailed description of some embodiments of the invention with reference to the accompanying drawings, wherein.

DETAILED DESCRIPTION OF THE INVENTION

Figure 1:
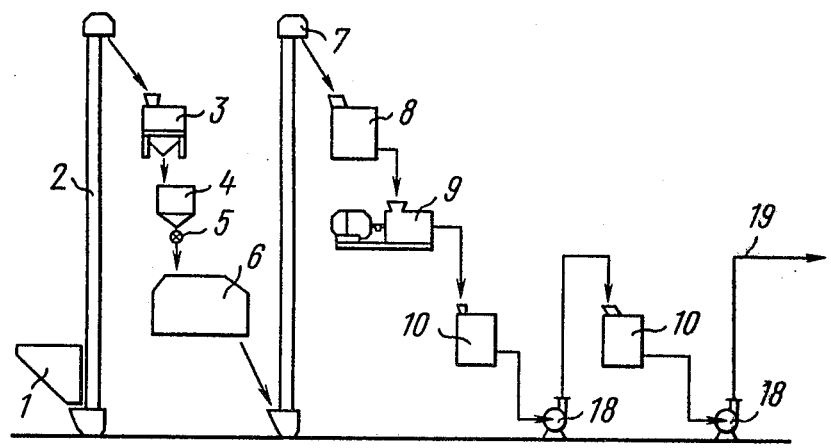
FIG. 1 is a flow-sheet of the apparatus for producing hydrolysates of a starch-containing feedstock according to the present invention.

The process for producing hydrolysates of a starch-containing feedstock according to the present invention is preformed in the following manner.

The starting starch-containing feedstock is delivered, after magnetic separation, to disintegration to a particle size of from 1 to 3 mm. The particle size is limited to this value due to the fact that particles with a size of below 1 mm during the subsequent extrusion are more liable to caramelization or burning and particles exceeding 3 mm size can hinder satisfactory extrusion, since in the case of passing along the extruder screw they can clog in the filier openings.

Then the disintegrated feedstock is delivered in a bulk stream into a receiving bin of the extruder and a continuous extrusion is effected while maintaining the temperature in the extruder cavity within the range of from 150° to 300° C. and pressure within the range of from $2.10^5$ to $2.10^8$ Pa with a pulse pressure release at the outlet from the zone.

Extrusion at a temperature below 150° C. gives poor-qualityextrudate, i.e. in such extrusion there is observed an incomplete destruction of cellular and intercellular shells of starch grains thus causing a poor hydrolysis of the extrudate, losses of sugars and lowering of the alcohol yield.

Extrusion at temperatures above 300° C. causes caramelization and burning of the starch and clogging of the openings in the extruder. In the first case irreversible losses of the starting feedstock take place, and in the second case, breakdown of the continuous extrusion process.

To avoid caramelization of the starch-containing feedstock and burning of starch and simultaneously provide for a good extrusion, the pressure created in the extruder (or, accordingly, the rate of passing of the feedstock through the working chamber) should be within the above-specified range depending on the chamber temperature.

The pressure below $2.10^5$ Pa lowers the rate of extrusion of the feedstock and, consequently affects the extruder productivity; it extends the time of residence of the feedstock in a hot chamber, thus increasing the probability of caramelization and burning of starch.

The pressure above $2.10^8$ Pa causes a sharp increase in power consumption for driving the extruder into rotation and reduces the optimal residence time of the feedstock in a hot chamber. In this case there is observed a break-through of the underextruded feedstock thus lowering the amount of soluble sugars and reducing the alcohol yield.

The resulting extrudate is poured with an aqueous enzymatic solution in a ratio of 1:3–4, for example with a solution of alpha-amylase, glucoamylase and subjected to hydrolysis at a temperature of 58°–60° C. for a period of from 3 to 60 minutes. The hydrolysis is carried out in an apparatus wherein opposite-direction vortical streams are created by means of a source of opposite-direction vortical streams forming such streams at a rotation speed of from 1,000 to 6,000 r.p.m. simultaneously with changing of their direction.

At a rotation speed of the source below 1,000 r.p.m. the line productivity sharply decreases, the process of the extrudate dissolution slows down and fails to be continuous.

The rotation speed above 6,000 r.p.m. is undesirable due to the fact that it does not actually influence the rate of treatment of the extrudate which corresponds, as to the required time, to the rotation speed of 6,000 r.p.m. Furthermore, there is a risk that at higher rotation speeds of the source, the latter can be broken. The speed of the source rotation below 1,000 and higher than 6,000 r.p.m. does not provide for turbulence conditions in the apparatus, whereby the hydrolysis intensity is substantially reduced.

It has been experimentally found that at the source rotation speed of about 6,000 r.p.m. the maximum hydrolysis is completed within 3 minutes, while at the rotation speed of 1,000 r.p.m. the hydrolysis is completed within one hour. Durtion of the hydrolysis beyond this time interval results in a lowered productivity of the apparatus.

The turbulization effect occurs because the mixture is treated in a closed apparatus with opposite-direction vortical streams resulting in elimination of the interphase liquid-gas boundary and the entire working volume is in a homogeneous phase state.

The process according to the present invention makes it possible to increase the amount of soluble sugars in hydrolysates of the starch-containing feedstock, intensity the process and increase the alcohol yield by at least 2%.

For a better understanding of the present invention some specific examples are given hereinbelow by way of illustration.

EXAMPLE 1

Corn is crushed to particles with a size of from 1 t 3 mm, passed through an extruder under the pressure of $2.0 \times 10^5$ Pa at the temperature of 170° C. for 2 seconds. Thereafter, the applied pressure is released in a pulse-like manner. The resulting extrudate is mixed with an aqueous solution of alpha-amylase in the ratio of 1:4 and fed into an apparatus for fermentative hydrolysis. The fermentative hydrolysis is conducted for 60 minutes with different-direction vortical streams at the rotation speed of the source of vortical streams of 1,000 r.p.m. The resulting hydrolysate contains 95% of soluble sugars.

EXAMPLE 2

Corn is crushed to particles with the size of 3 mm, passed through the extruder under the pressure of $2.10^6$ Pa at the temperature of 200° C. for 6 seconds. Thereafter the applied pressure is released in a pulse-like manner. The resulting extrudate is mixed with an aqueous solution of alpha-amylase in the ratio of 1:3 and subjected to fermentative hydrolysis as in Example 1 for 3 minutes at the rotation speed of the source of opposite-direction vortical streams of 6,000 r.p.m.

The resulting hydrolysate contains 96% of soluble sugars.

EXAMPLE 3

Wheat is crushed to particles with a size of 2-3 mm, passed through an extruder under the pressure of $1.10^6$ Pa at the temperature of 150° C. for 6 seconds. Thereafter the applied pressure is released in a pulse-like manner. The resulting extrudate is mixed with an aqueous solution of alpha-amylase in the ratio of 1:3 and subjected to fermentative hydrolysis as in Example 1 for 20 minutes at the speed of rotation of the source of opposite-direction vortical streams of 1,500 r.p.m.

The resulting hydrolysate 96% of soluble sugars.

EXAMPLE 4

Rice is crushed to particles of a size of from 2 to 3 mm, passed through an extruder under the pressure of $1.5 \times 10^6$ Pa at the temperature of 130° C. for 2 seconds. Then the applied pressure is released in a pulse-like manner. The resulting extrudate is mixed with an aqueous solution of alpha-amylase and glucoamylase in the ratio of 1:3 and subjected to the fermentative hydrolysis as in Example 1 for 10 minutes at the speed of rotation of the source of opposite-direction streams of 1,500 r.p.m The resulting hydrolysates contains 96% of soluble sugars.

EXAMPLE 5

Barley is crushed to particles with a size of 2-3 mm and passed throughan extruder under the pressure of $2.10^5$ Pa at the temperature of 160° C. for 2 seconds. Then the pressure is released in a pulse-like manner. The resulting extrudate is mixed with an aqueous solution of alpha-amylase in the ratio of 1:3 and subjected to fermentative hydrolysis as described in Example 1 for 30 minutes at the speed of rotation of the source of opposite-directions vortical streams of 3,000 r.p.m.

The resulting hydrolysate contains 96% of soluble sugars.

EXAMPLE 6

Rye is crushed to particles with a size of 1-2 mm and passed through an extruder under the pressure of $2.10^6$ Pa at the temperature of 140° C. for 2 seconds.

Then the pressure is released in a pulse-like manner. The resulting extrudate is mixed with alpha-amylase in the ratio of 1:4 and delivered to the fermentative hydrolysis similar to that described in Example 1 at the speed of rotation of the source of opposite-direction vortical streams of 1,400 r.p.m. for 40 minutes.

The resulting hydrolysate contains 96% of soluble sugars.

EXAMPLE 7

Oats is crushed to a particle size of 1-2 mm and passed through an extruder under the pressure of $2.10^8$ Pa at the temperature of 150° C. for 2 seconds. Then the pressure is released ina pulse-like manner. The resulting extrudate is mixed with an aqueous solution of alpha-amylase in the ratio of 1:3 and subjected to the fermentative hydrolysis as in Example 1 for 5 minutes at the speed of rotation of the source of opposite-direction votical streams of 5,000 r.p.m.

The resulting hydrolysate contains 96% of soluble sugars.

As control for all the Examples use is made of a conventional method for preparation of a starch-containing raw material for an alcoholic fermentation. In the following Table there are given comparative data illustrating the yield of ethanol from 1 ton of starch.

| Example No. | Control, dl | Experiment, dl | Yield increase, dl |
|---|---|---|---|
| 1 | 63.93 | 66.24 | 2.31 |
| 2 | 63.96 | 67.98 | 4.02 |

An apparatus for the production of hydrolysates of a starch-containing feedstock by the process according to the present invention comprises a receiving bin 1 (FIG. 1), a conveyor 2, balance 3, intermediate bin 4, feeder 5, separator 6 for separation of foreign matter, conveyor 7, crusher 8, extruder 9, consisting of a housing with a control panel, a receiving bin and a screw mechanism (not shown). Extruder 9 is connected with means 10 for fermentative hydrolysis, consisting of a cylindrical vessel 11 (FIG. 2) and a cover 12. Inside the cylindrical vessel 11 there is mounted a source of opposite-direction vortical streams comprising at least two horizontally mounted perforated discs 13; one of them is rigidly secured to the inner surface of the cylindrical vessel 11 and the other is mounted under the first disc in close vicinity thereto and rigidly fixed on a shaft 14 rotatably mounted along the axis of the cylindrical vessel 11 and at least six ribs 15 for changing the direction of vortical streams of the mixtures. Three of these ribs 15 are rigidly fixed on the inner surface of the cylindrical vessel 11 parallel to its axis and three other ribs are radially mounted on the cover 12.

The cylindrical vessel 11 is provided with a conduit 16 for the mixture supply and a conduit 17 for the mixture removal.

In the apparatus there can be mounted several similar means for the fermentative hydrolysis.

Figure 2:
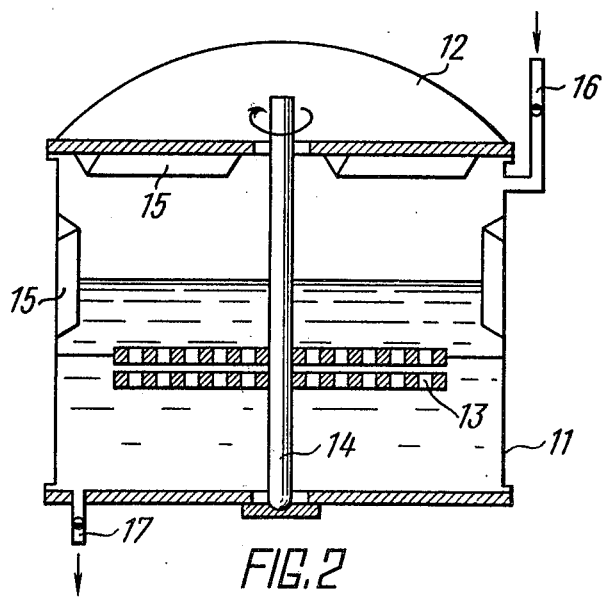
FIG. 2 is a schematic view of the apparatus for the fermentative hydrolysis according to the present invention.

The mixture is pumped to fermentation and from one means to another by means of pumps 18 (FIG. 1).

The apparatus for producing hydrolysates of a starch-containing feedstock for the alcoholic fermentation operates in the following manner.

A starch-containing feedstock such as grain is fed into a receiving bin 1, from which by means of a conveyor 2 it is fed to balance 3. The weighed portion of the grain is charged into an intermediate bin 4 connected with a feeder 5. From the feeder the grain is delivered to a separator 6 for separation of foreign impurities, whereafter it is transported by a conveyor 7 into a crusher 8, wherein the grain is crushed to particles with a size of from 1 to 3 mm.

The crushed feedstock is passed through an extruder 9, wherein it is subjected to a heat-mechanical treatment at a temperature of from 150° to 300° C. under a pressure of from $2.10^5$ to $2.10^8$ Pa. The resulting extrudate is fed, via the conduit 16, into means 10 for the fermentative hydrolysis, wherein owing to rotation of the discs 13 (FIG. 2) fixed on shaft 14 vortexes of the mixture are created simultaneously with change of their direction by means of ribs 15.

The mixture is continuously circulated through the perforated stationary and mobile discs 15 and in the clearance therebetween the mixture is subjected to dispersing.

After the fermentative hydrolysis the mixture is pumped, through the conduit 17, by means of pump 18 to the means similar to that described hereinabove and then pumped by pump 18 via the conduit 19 to the fermentation (the fermentation unit is now shown in the drawings).

What is claimed is:

1. A process of producing hydrolysates of a starch-containing feedstock for alcoholic fermentation, which comprises disintegrating a starch-containing feedstock to a particle size of 1 to 3 mm;

extruding the disintegrated feedstock at a temperature of from 150° to 300° C. under a pressure of $2.10^5$ to $2.10^8$ Pa;

mixing the resulting extrudate with an aqueous enzymatic solution in a ratio of 1:3–4;

subjecting the resulting mixture to fermentative hydrolysis for 3 to 60 minutes under the action of opposite-direction vortical streams of said mixture created by opposite-direction vortical streams of said mixture created by opposite- direction vortical streams formed by discs rotating at a rotation speed of 1,000 to 6,000 r.p.m. with changing of their direction.

* * * * *